United States Patent
DeMan et al.

(10) Patent No.: US 8,031,828 B1
(45) Date of Patent: Oct. 4, 2011

(54) METHOD AND APPARATUS FOR COMPUTED TOMOGRAPHY

(75) Inventors: Bruno Kristiaan Bernard DeMan, Clifton Park, NY (US); Jiang Hsieh, Brookfield, WI (US); Jed Douglas Pack, Glenville, NY (US); Kai Zeng, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/771,875

(22) Filed: Apr. 30, 2010

(51) Int. Cl.
*A61B 6/00* (2006.01)
(52) U.S. Cl. .............................. 378/4; 378/15
(58) Field of Classification Search .................. 378/4, 15
See application file for complete search history.

(56) References Cited

U.S. PATENT DOCUMENTS

| | | | |
|---|---|---|---|
| 4,442,489 A * | 4/1984 | Wagner | 378/19 |
| 5,970,112 A | 10/1999 | Hsieh | |
| 6,014,419 A * | 1/2000 | Hu | 378/4 |
| 6,041,097 A * | 3/2000 | Roos et al. | 378/62 |
| 6,307,912 B1 | 10/2001 | He et al. | |
| 6,385,278 B1 * | 5/2002 | Hsieh | 378/8 |
| 6,445,761 B1 * | 9/2002 | Miyazaki et al. | 378/8 |
| 6,546,067 B2 * | 4/2003 | Aradate et al. | 378/15 |
| 7,542,792 B2 | 6/2009 | Wollenweber et al. | |
| 2005/0226484 A1 | 10/2005 | Basu et al. | |
| 2006/0034417 A1 * | 2/2006 | Katsevich | 378/4 |
| 2007/0116171 A1 * | 5/2007 | Hsieh et al. | 378/8 |
| 2007/0147576 A1 * | 6/2007 | Yamazaki | 378/4 |
| 2007/0147579 A1 | 6/2007 | DeMan et al. | |
| 2009/0262885 A1 * | 10/2009 | Bontus et al. | 378/11 |

FOREIGN PATENT DOCUMENTS

JP 2008018044 1/2008

OTHER PUBLICATIONS

Bontus, Claas, et al.; "Circular CT in Combination with a Helical Segment," Phys. Med. Biol. 52 (2007) pp. 107-120.
U.S. Appl. No. 12/714,168, filed Feb. 26, 2010, Abdelaziz Ikhlef et al.

* cited by examiner

*Primary Examiner* — Edward Glick
*Assistant Examiner* — Alexander H Taningco
(74) *Attorney, Agent, or Firm* — Fletcher Yoder

(57) ABSTRACT

In one embodiment, a first set of projection data is acquired using a first portion of a detector and a second set of projection data is acquired using a second portion of the detector. The second set of projection data is supplemented based upon the first set of projection data to generate a supplemented set of projection data. A volumetric image may be generated using the supplemented set of projection data.

20 Claims, 8 Drawing Sheets

METHOD AND APPARATUS FOR COMPUTED TOMOGRAPHY

BACKGROUND OF THE INVENTION

The invention relates generally to medical imaging and, in particular, to the acquisition and/or reconstruction of images using computed tomography.

Non-invasive medical imaging technologies allow a caregiver to obtain and view images of the internal structures and organs of a patient without performing surgery or other invasive procedures. In particular, technologies such as X-ray radiography, computed tomography (CT), tomosynthesis, magnetic resonance imaging (MRI), ultrasound, C-arm angiography, positron emission tomography (PET), and single positron emission computed tomography (SPECT) use various physical principles to create two-dimensional and/or three-dimensional representations of the interior of the human body. For example, in those imaging modalities utilizing X-rays, the principle of operation typically involves assessing the differing attenuation of the X-rays by the patient's body at one or more angles. Based upon the differential attenuation attributable to different tissues, a two- or three-dimensional image may be reconstructed that accurately depicts the internal structure of the patient. Different imaging modalities apply differing physical principles, but in each case a useful image derived using some property of the patient's body is produced.

In CT, one or more X-ray sources are typically employed which are rotated about a patient (or other object undergoing imaging) to collect X-ray attenuation data at a variety of angular positions. For scans in which data is collected over a wide viewing area (i.e., where the X-ray beam is emitted as a wide cone) attenuation data may be missing or incomplete due to longitudinal data truncation at the edges of the detector. Likewise, certain types of image artifacts (e.g., cone beam artifacts) may be introduced in systems where X-rays impact the detector at wide cone angles. Likewise, image artifacts may occur when the X-ray beam is not wide enough to cover the entire cross-section of the object being scanned, resulting in transaxial data truncation. Such artifacts and missing data may reduce the usefulness of images acquired using such systems.

BRIEF DESCRIPTION OF THE INVENTION

In one embodiment, a method is provided. In accordance with the method, a first set of projection data is acquired using a first portion of a detector and a second set of projection data is acquired using a second portion of the detector. The first portion is shaped differently than the second portion. The second set of projection data is supplemented based upon the first set of projection data or data derived using the first set of projection data to generate a supplemented set of projection data. A volumetric image is generated using the supplemented set of projection data.

In another embodiment, a method is provided. In accordance with the method, a set of helical scan projection data is acquired using a first portion of a detector and an X-ray beam collimated to a first cone angle. A set of axial scan projection data is acquired using a second portion of the detector and an X-ray beam collimated to a second cone angle that is wider than the first cone angle. A set of synthesized data is generated using the set of helical scan projection data. The set of axial scan projection data is supplemented using all or part of the set of synthesized data. A volumetric representation is generated using the supplemented set of axial scan projection data.

In a further embodiment, one or more computer-readable media comprising code adapted to be executed on a processor are provided. The code includes code that, when executed on the processor, causes a first set of projection data to be acquired using a first scan protocol and a first portion of a detector. The code also includes code that, when executed on the processor, causes a second set of projection data to be acquired using a second scan protocol and a second portion of the detector. The second scan protocol differs from the first scan protocol and the second portion of the detector differs from the first portion of the detector. The code also includes code that, when executed on the processor, causes the second set of projection data to be supplemented using the first set of projection data or data generated using the first set of projection data. The code also includes code that, when executed on the processor, causes a volumetric representation to be generated using the supplemented second set of projection data.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present techniques are directed to the identification of different anatomical and/or pathological structures in medical images. The technique may be useful for distinguishing between certain types of tissues in different organs. For example, the present disclosure may be useful in distinguishing between lung nodules and healthy lung tissue. Likewise, the techniques may be useful for diagnosing coronary artery disease or for identifying other tissue types associated with other organs. In one embodiment, shape-based descriptors are used classify elements of an image (such as voxels in a three-dimensional representation) as different tissue types of interest. In this manner, different structural elements within an image may be labeled in accordance with the type of tissue they represent.

Figure 1:
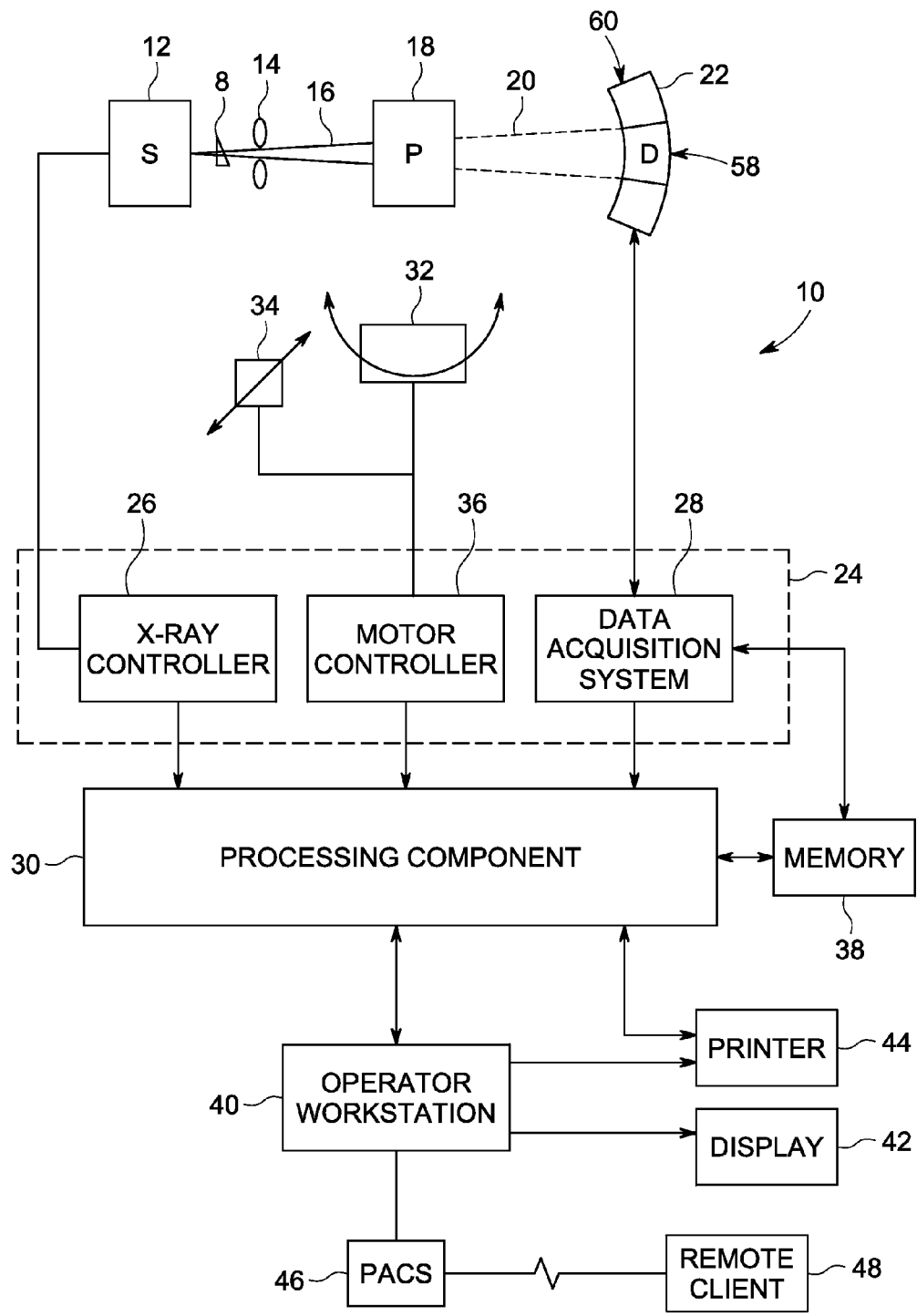
FIG. 1 is a system-level view of an exemplary imaging system in the form of a CT imaging system in accordance with embodiments of the present disclosure.
Figure 2:
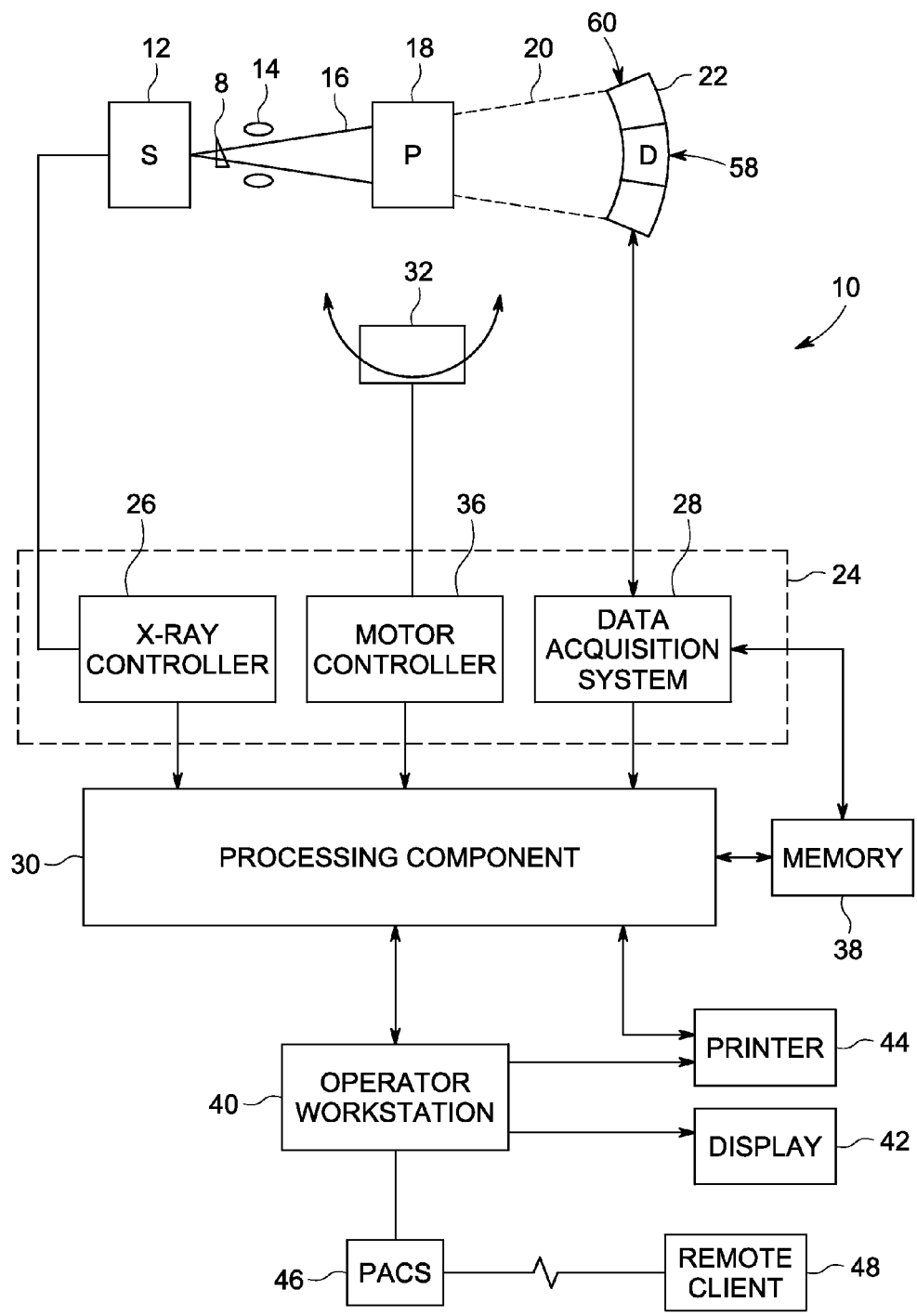
FIG. 2 is a system-level view of an exemplary imaging system in the form of a CT imaging system in accordance with further embodiments of the present disclosure.

With this in mind, an example of a computer tomography (CT) imaging system that may be used to acquire images processed in accordance with the present techniques is provided in FIGS. 1 and 2. In the depicted embodiment, an imaging system 10 in the form of a CT system is provided to acquire X-ray attenuation data at a variety of views around a volume undergoing imaging (e.g., a patient, package, manufactured part, and so forth). In the embodiment illustrated in FIGS. 1 and 2, the imaging system 10 includes a source of X-ray radiation 12 configured to emit radiation (e.g., X-rays 16) through a volume containing a subject (e.g. patient 18) or object undergoing imaging. In the depicted embodiment, the emitted X-rays 16 pass through an adjustable collimator 14 that limits the angular range associated with the X-rays 16 passing through the volume in one or more dimensions, as depicted in FIGS. 1 and 2. In addition, the emitted X-rays 16 may pass through one or more filters, such as a bowtie filter 8, to adjust frequency and/or intensity characteristics of the emitted X-rays 16.

With respect to these system components, the X-ray source 12 may include one or more X-ray emitting structures, such as one or more X-ray tubes, one or more distributed X-ray sources (e.g., array X-ray sources, such as a solid-state or thermionic X-ray source) or any other X-ray emitting structures suitable for generating X-rays to pass through the imaging volume. In embodiments in which more that one X-ray emitting structure (e.g., X-ray tubes) is present, the emitting structures may be displaced from one another azimuthally (i.e., along the circumference of the scanner), axially (i.e., along the rotational axis of the scanner or along the Z-axis), or both azimuthally and axially. Further, as discussed below, in embodiments in which more that one X-ray emitting structure (e.g., tubes) is present, the emitting structures may be separately or differentially collimated to illuminate different detectors or detector regions. In addition, an X-ray emitting structure or more than one such X-ray emitting structure may be operated at different power (e.g., 60 kW and 100 kW) to allow dual- or multi-energy imaging or material discrimination. As will be appreciated, in embodiments in which more than one X-ray emitting structure is present, the different X-ray emitting structures may be different types of structures (e.g., one X-ray source may be of a rotating anode type structure while another may be a field emission source).

The collimator 14 shapes the emitted X-rays 16 to a generally cone or generally fan shaped beam that passes into and through the imaging volume in which the subject or object of the imaging process (e.g., patient 18) is positioned. As discussed herein, the collimator 14 may be adjusted to accommodate different scan modes, such as to provide a narrow X-ray beam (such as a generally fan-shaped beam) in a helical scan mode and a wider X-ray beam (such as a more cone-shaped beam) in an axial scan mode. In one embodiment, the collimator 14 may be formed from two hinging cylindrical disks (e.g., conventional or custom-shaped cams), as depicted in FIGS. 1 and 2, that rotate to adjust the shape or angular range of the X-ray beam that passes through the imaging volume. In another embodiment, the collimator 14 may be formed using two or more translating plates (e.g., shutters). In one embodiment, the collimator 14 may be formed such that an aperture defined by the collimator 14 corresponds to a shape of a radiation detector, discussed below. Further, in one embodiment, the collimator 14 may actually include multiple collimating elements that perform the collimation in different dimensions and/or for different regions of the detector. For example, in one embodiment a standard cam-type arrangement may collimate X-rays along the Z-axis, a shutter-type arrangement may collimate X-rays in the X-dimension (i.e., orthogonally with respect to the Z-axis and defining the field of view of the scanner), and/or a fixed filter may eliminate or block X-ray photons directed toward the corner regions which may be missing in some detector embodiments, as discussed below.

With respect to the bowtie filter 8, in certain embodiments the bowtie filter 8 may be a conventional bowtie filter or other X-ray beam shaping filter suitable for varying the intensity of the beam of X-rays 16 to compensate for different thicknesses of the patient 18 as seen from different angular positions of the X-ray source 12. In one embodiment, the thickness of the bowtie filter 8 may vary in the axial direction to compensate for the Heel effect. Alternatively a separate or additional filter whose thickness varies in the axial direction may be provided in conjunction with the bowtie filter 8 to compensate for the Heel effect.

As depicted in FIGS. 1 and 2, a portion of the X-ray radiation 20 passes through or around the patient 18 and impacts one or more detector arrays, represented generally at reference numeral 22. Detector elements 54 (FIGS. 3 and 4) of the array or arrays produce electrical signals that represent the intensity of the incident X-rays 20. These signals are acquired and processed to reconstruct images of the features within the patient 18.

Figure 3:
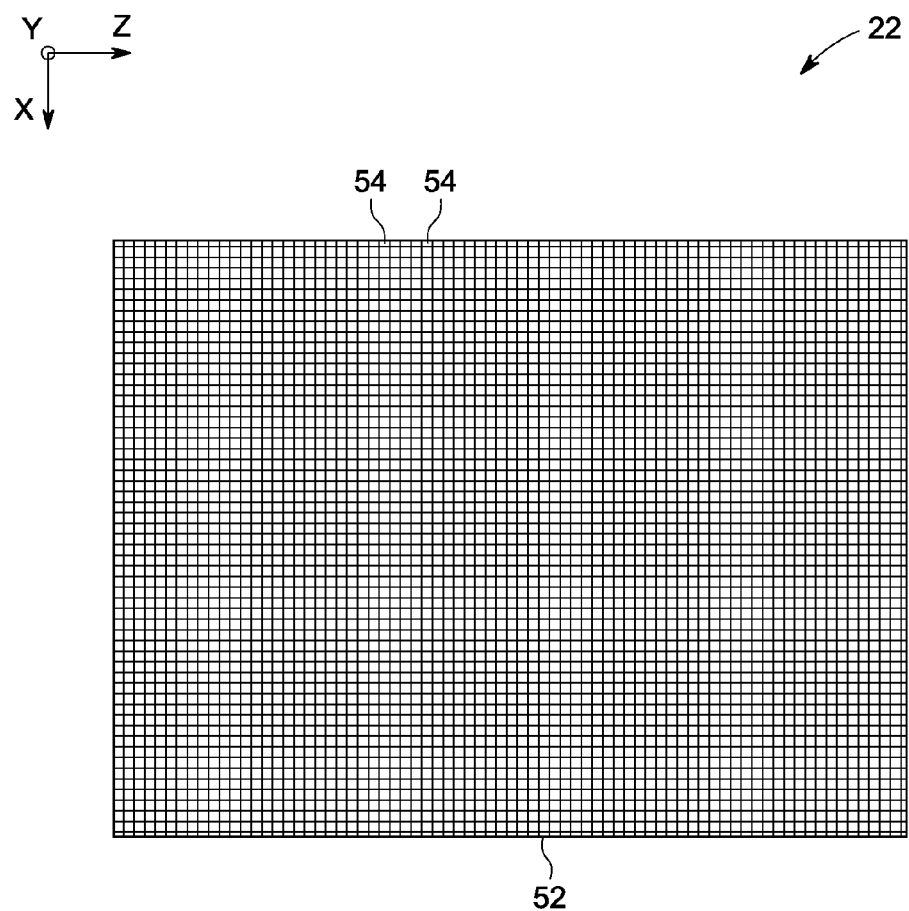
FIG. 3 is a plan view of a detector suitable for use in accordance with the present disclosure.

In one embodiment, the detector 22 may be provided as one or more as a flat surface or as a curviplanar surface with a focus at the X-ray source 12. In one such embodiment, the detector 22 may be a square or rectangular detector 52 comprised of one or more arrays of discrete detector elements 54, as depicted in the embodiment of FIG. 3. In such an embodiment, portions of the square or rectangular detector 52 (such as the corner portions) may not be illuminated by X-rays or may be subject to limited or reduced illumination, such as due to collimation by the collimator 14, during all or part of a scan. Similarly, portions of the square or rectangular detector 52 (such as the corner portions) may not be read out or may be read out at a reduced frequency during all or part of a scan.

Figure 4:
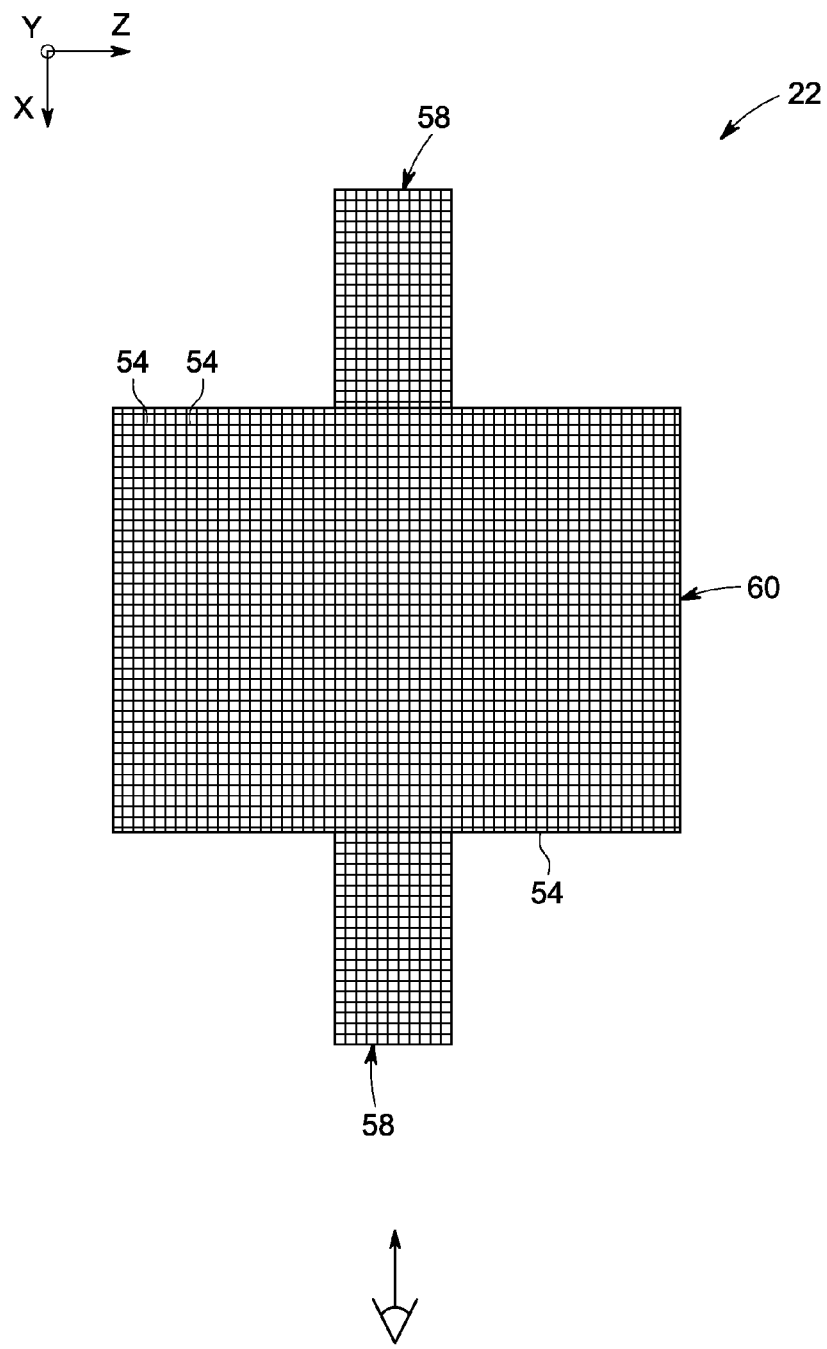
FIG. 4 is a plan view of an alternative detector suitable for use in accordance with the present disclosure.

Alternatively, in another such embodiment, the detector 22, may be provided in a non-square or non-rectangular shape, such as an asymmetrically shaped or a cross-shaped detector 56, as depicted in FIG. 4. In one such embodiment, the cross-shaped detector 56 may include an elongated or wide portion 58 corresponding to a wide field of view (i.e., the size of the scanned circular cross section) and a reduced extent in the Z-dimension such that there is a relatively narrow cone angle in the Z-dimension. Such a wide portion may be illuminated when the X-rays 16 are collimated to a generally fan-shaped beam having a limited Z-coverage (such as from −0.5° to +0.5° for 1° of coverage) but extensive X-coverage (i.e., an extensive field of view), as depicted in FIG. 1. In one such embodiment, the wide portion 58 is illuminated with X-rays 16 collimated in such a fan-shape during a helical-scan protocol in which the patient 18 is translated in the Z-direction during image data acquisition. While FIG. 4 depicts a cross-shaped detector 56 having a wide portion 58 that extends outward from the central portion 60 (see below) in two directions (i.e., on two sides), in other embodiments the wide portion 58 may only extend outward in from one side of the central portion 60, i.e., the detector may be asymmetric.

In a related embodiment, the cross-shaped detector 56 may include a central portion 60 corresponding to a reduced field of view (referring to the size of the scanned circular cross-section) and an increased extent in the Z-dimension such that there is a relatively wide cone angle in the Z-dimension. Such a central portion 60 may be illuminated when the X-rays 16 are collimated to a generally cone-shaped beam having a limited X, Y-coverage (i.e., field of view) but extensive Z-coverage (such as from −6° to +6° for 12° of coverage), as depicted in FIG. 2. In one such embodiment, the central portion 60 is illuminated with X-rays 16 collimated in such a cone-shape during an axial-scan protocol in which the patient 18 is not translated in the Z-direction during image data acquisition.

In one embodiment, the detector 22 may be formed using modular construction such that different modular arrays of detector elements may be connected to form the cross-shaped, asymmetric, square, or rectangular detector array. For example, in the case of a cross-shaped detector 56, one or more modular arrays of elements 54 may be connected to form the central portion 60 while additional modular arrays of elements 54 may be connected to the sides of the central portion 60 to form the wide portions 58. Further, in one embodiment, the modular arrays of elements may be connected using a hinged or rotatable assembly such that different modules may be rotated with respect to one another, such as to allow reconfiguration or reshaping of the detector from one shape, such as square, to another, such as rectangular.

With respect to resolution, the detector 22 may have a common or uniform resolution or may have different regions or elements 54 that have different resolutions and/or cell size relative to the remainder of the detector 22. For example, in one embodiment in which the detector 22 is a cross-shaped detector 56, the central portion 60 may be composed of detector elements having higher spatial resolution and/or smaller cell size than the detector elements composing the wide portions 58.

The detector 22 may include various other properties and/or functions. For example, in certain embodiments, the detector 22 may be an energy-integrating detector, an energy-discriminating multi-layer detector, a photon-counting detector, an energy-discriminating photon-counting detector, or some combination of these. In addition, different regions of the detector 22 may provide different types of functionalities of the types listed above. For example, in a cross-shaped detector 56, the central portion 60 may include photon-counting and/or energy-discriminating functionality, one or both of which may be absent in the wide portions 58 extending outward from the central portion 60. Conversely, in such an embodiment, the wide portions 58 may provide energy-integrating functionality that may be absent in the central portion 60.

Further, all or portions of the detector 22 may be associated with or include an anti-scatter grid to absorb or otherwise prevent X-ray photons that have been deflected or scattered in the imaging volume from impacting the detector 22. Such an anti-scatter grid may be one- or two-dimensional and/or may consist of multiple sections, some of which are one-dimensional and some of which are two-dimensional. In addition, in certain embodiments in which more than one X-ray source 12 is present, an anti-scatter grid may consist of multiple sections, with different sections focused at different X-ray sources. In one embodiment, detector regions corresponding to a generally fan-shaped X-ray beam may have two-dimensional collimation directed to a single-spot, high-power rotating anode tube source while detector regions corresponding to a wide-cone X-ray beam may be provided with laminar collimation to a multi-spot source configuration arrayed in the Z-direction of the imaging system 10.

With the foregoing components and features of the imaging system 10 in mind, and returning to FIGS. 1 and 2, the X-ray source 12 is typically controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIGS. 1 and 2, system controller 24 is coupled to a rotational subsystem 32 and/or a linear positioning subsystem 34. The rotational subsystem 32 enables the X-ray source 12, collimator 14 and the detector 22 to be rotated one or multiple turns around the patient 18. It should be noted that the rotational subsystem 32 might include a gantry upon which the respective X-ray emission and detection components are disposed. Thus, in such an embodiment, the system controller 24 may be utilized to operate the gantry. The linear positioning subsystem 34 may enable the patient 18, or more specifically a table supporting the patient, to be displaced within the bore of the CT system 10. Thus, the table may be linearly moved within the gantry to generate images of particular areas of the patient 18. In the depicted embodiment, the system controller 24 controls the movement of the rotational subsystem 32 and/or the linear positioning subsystem 34 via a motor controller 36. In the embodiment depicted in FIG. 2, the linear positioning subsystem 34 is omitted from the illustration to reflect that, in certain scan protocols, such as axial scan protocols, the patient may remain stationary (i.e., is not linearly displaced) during image data acquisition. In such embodiments, the linear positioning subsystem 34 may still be present, and indeed, may translate the patient 18 before and/or after the axial scan. In other embodiments, the linear positioning subsystem 34 may translate the patient 18 at non-constant speed to achieve a heli-axial trajectory. For example, the linear positioning subsystem 34 may translate the patient at a decelerating speed, coming to a stop at a point where the axial scan is performed, before resuming translation of the patient at an accelerating speed to finish the helical scan. Thus, the translation speed may vary depending on the scan protocol or the point within a scan protocol.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that a plurality of radiographic views may be collected for processing. In the present context, system controller 24 may also includes signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for iterative image reconstruction described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the present approaches. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

With the foregoing example of one suitable image acquisition system in mind, acquiring and processing image data in accordance with certain protocols are now discussed. For example, in one embodiment, the system 10 discussed above is used to acquire image data using two different and distinct scans during a single examination. In one such example, the X-rays 16 emitted in the first scan are collimated to have a large or full field of view (i.e., a large or full scanned circular cross-section) but a narrow extent in the Z-dimension. For example, the X-rays 16 may be collimated to a generally fan-shaped beam with a narrower cone angle in the Z-dimension. In addition, in one implementation the X-rays 16 use in the first scan may constitute a low-dosage (e.g., generated at a tube current of about 20 mA). Conversely, X-rays 16 emitted during the second scan are collimated to have a larger extent in the Z-dimension and possibly a reduced or limited field of view. For example, the X-rays may be collimated to a generally cone-shaped beam with a wider cone angle in the Z-dimension. In one implementation the X-rays 16 use in the second scan may constitute a higher-dosage (e.g., generated at a tube current of about 500 mA).

In one embodiment, information obtained using the first scan may be used to extract (automatically or with user involvement) some information about patient position, placement, size, shape, and/or density. Such extracted information may be used to select a region of interest for the second scan and/or to define the table positioning in order to center the projected region of interest onto the detector 22 for the second scan. Furthermore, in certain embodiments the data obtained using the first scan may be used to set the X-ray source kVp and/or mA modulation, bowtie filter configuration, and/or detector view rate for the second scan to achieve suitable tissue contrast, noise index, and/or dose based on the selected protocol settings. Further, data from the first scan may also be used to correct for scatter and/or cone-beam artifacts and/or truncation artifacts in the second scan.

Further, the first scan can be used to compute patient attenuation maps and/or patient organ maps. Such maps may be subsequently used to compute image noise and/or patient dose as a function of mA and/or kVp modulation. Further such maps may be used to compute image contrast as a function of kVp modulation. In addition, such maps may be used to compute a desired mA and/or kVp modulation profile for subsequent scans.

Figure 5:
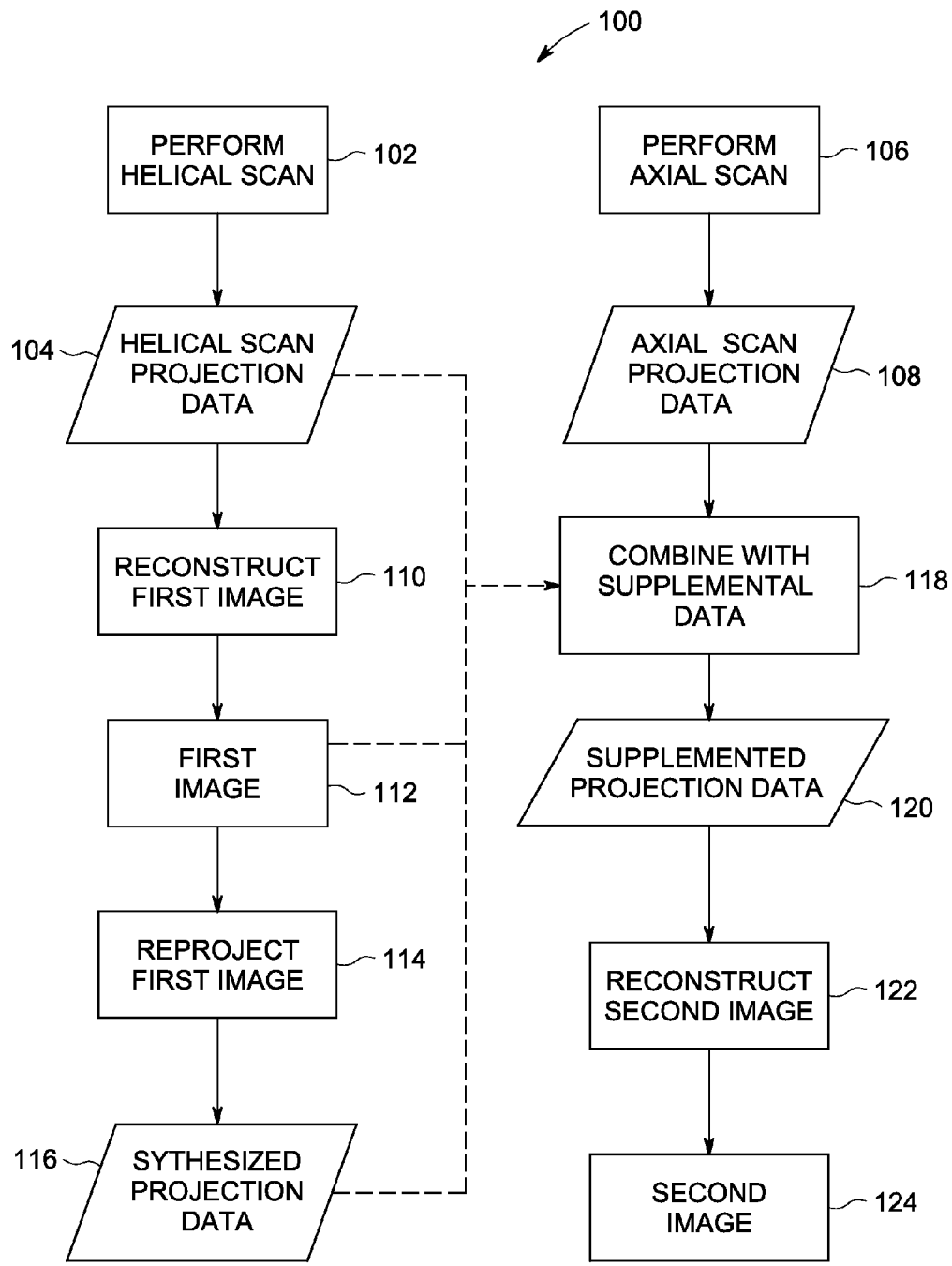
FIG. 5 is a flowchart depicting control logic suitable for implementing one embodiment of an image acquisition and processing algorithm in accordance with the present disclosure.

With this in mind, and turning to FIG. 5, a method 100 is depicted having control logic that can be implemented for performing two distinct types of scans during an examination. In such an example, the first scan may be a helical scout scan 102 in which a low-dose, generally fan-shaped X-ray beam is rotated about the patient 18 while the patient 18 is translated through the imaging volume (i.e., the gantry bore). Such a helical scout scan may be associated with low or reduced scatter effects and low or reduced incidence of cone beam artifacts (due to the tighter collimation and limited extent of the X-ray beam in the Z-dimension). In one such implementation, such a helical scout scan may have 40 mm of coverage in the Z-dimension with a 50 cm field of view (corresponding to the surface of a cylinder having a 50 cm diameter). Helical scan projection data 104 is generated as a product of the helical scan.

As will be appreciated, the described helical scout scan differs from a conventional scout scan in that the source 12 and detector 22 are rotated about the patient 18 during image acquisition. In a conventional scout scan, the scan may occur at low dose, as with the helical scout scan, but the source 12 and detector 22 are not rotated. Instead, in the conventional scout scan data is collected in one or two passes, with the source 12 and detector 22 offset by some amount (such as 90°) between passes. Thus, in a conventional scout scan, the acquired data is two-dimensional projection data acquired at one or two different angular offsets. As will be appreciated, such a conventional scout scan may be performed in addition to or to supplement the scan protocols discussed herein to provide additional image projection data that may be used in performing the scan operations or in the image processing and reconstruction processes described herein.

In the depicted example, the second scan may be an axial scan 106 in which a higher-dose, generally cone-shaped X-ray beam is rotated about the patient 18 while the patient is stationary in the imaging volume (i.e., the gantry bore). Alternatively, a step-and-shoot protocol may be used in conjunction with axial scan such that the patient 18 is translated in a step-wise manner between axial rotations of the X-ray source 12 and detector 22 such that contiguous slabs or slices of image data are acquired by the axial scans. In one such implementation, a rotation of the source 12 and detector 22 about the imaging volume occurs in about 0.35 seconds. In one embodiment, such an axial scan may provide a field of view corresponding to partial or full coverage for an organ (such as full cardiac coverage) for acquiring image data related to the organ in a full scan protocol (e.g., a full rotation about the patient) or a partial or half scan protocol (e.g., a partial rotation of 180°+α (where α corresponds to the field of view angle of the X-ray beam)). Further, such an axial scan may be suitable for imaging dynamic processes, such as a beating heart. While, for the sake of explanation, the first scan has been denoted the helical scan and the second scan has been denoted the axial scan, it should be appreciated that this is merely to differentiate the scans, and does not imply an order in which the scans are necessarily performed. That is, the helical scan may be performed before or after the axial scan. Or the helical scan could even be split in two portions, with one portion performed before and one portion performed after the axial scan.

Such an axial scan may be associated with scatter effects and cone beam artifacts (due to the wide collimation and extended extent of the X-ray beam in the Z-dimension). In one such implementation, such an axial scan may have 120 mm-160 mm of coverage in the Z-dimension with a 25 cm-30 cm field of view (corresponding to the surface of a cylinder having a 50 cm diameter). Axial scan projection data 108 is generated as a product of the axial scan.

In such an embodiment, limited field of view used in the axial scan 106 yields axial scan projection data 108 that is truncated, i.e., there is incomplete or missing data corresponding to where the field of view was limited during the axial scan. In one embodiment, a portion of the helical scan projection data 104 may be used directly or may be extrapolated to fill in the truncated data that is absent in the axial scan projection data 108.

In one embodiment, the helical scan projection data 104 may be reconstructed (block 110) to generate a first image 112 that is a volumetric representation (i.e., three-dimensional representation) of the volume imaged by the helical scan. In this embodiment, the first image 112 is used to reproject (block 114) the first image 112 based on the geometry and/or parameters used or to be used in performing (block 106) the axial scan. Thus, based on the reprojection step 114, a set of synthesized projection data 116 is generated that may be used or combined (block 118) with the axial scan projection data 108 to generate a set of supplemented projection data 120 that includes some or all of the truncated data that is otherwise missing from the axial scan projection data 108. The supplemented projection data 120 may then be reconstructed (block 122) to generate a second image 124 with better noise and/or cone-beam artifact characteristics than might otherwise be generated using the axial scan projection data alone. Alternatively, in other embodiments, the synthesized projection data 116 may be generated directly from the helical scan projection data 104 (without a reconstruction and reprojection step) in the projection domain through interpolation and rebinning. Further, in other embodiments, the reconstructed images 112 from the helical scan can be transformed or processed in other ways to supplement the axial scan data.

Figure 6:
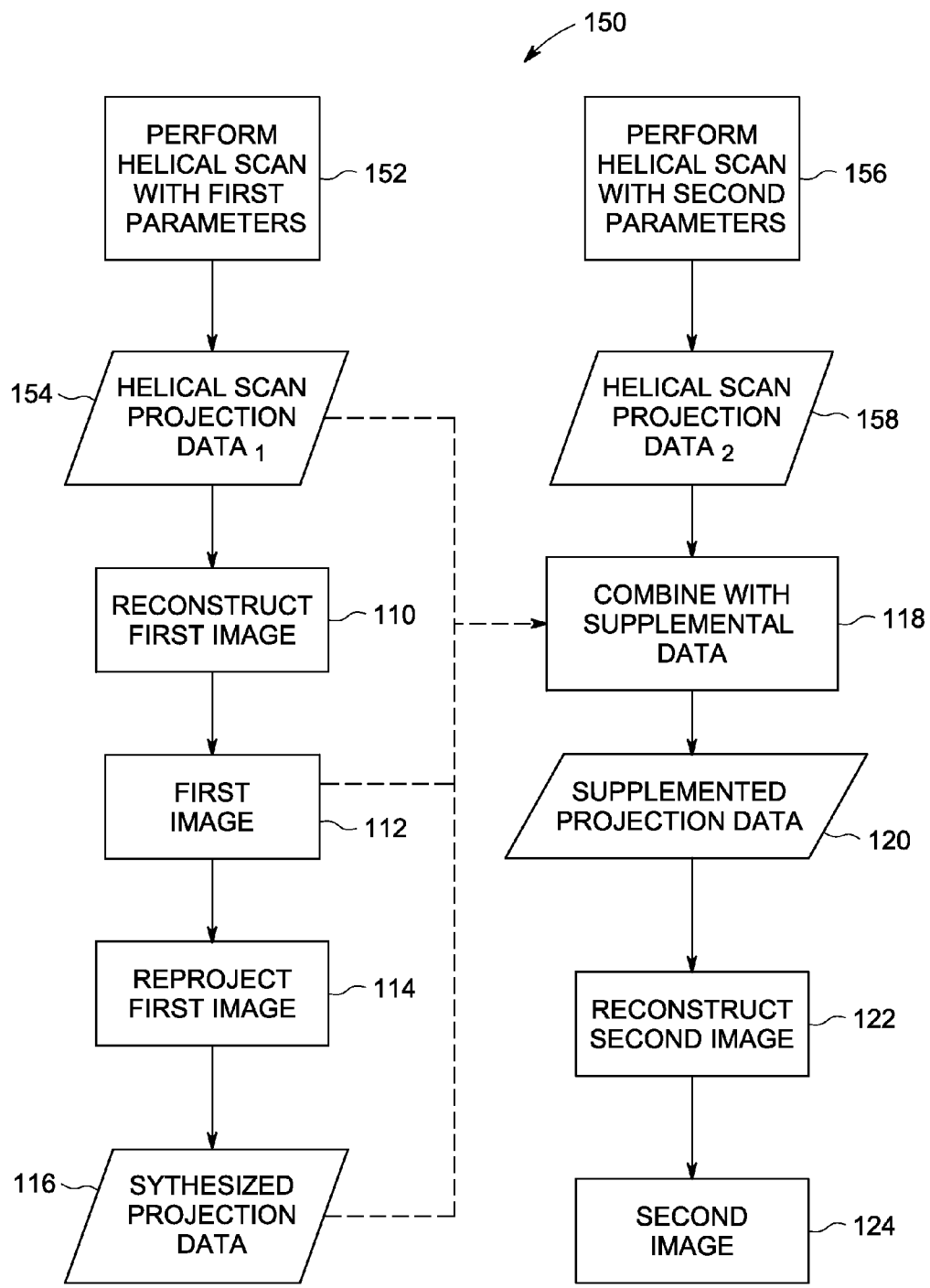
FIG. 6 is a flowchart depicting control logic suitable for implementing another embodiment of an image acquisition and processing algorithm in accordance with the present disclosure.

Turning now to the method 140 depicted in FIG. 6, in an alternative embodiment, the first and second scans may both be helical scans. In one such embodiment, the first helical scan may be performed (block 152) as discussed above with a full field of view and narrow Z-coverage (e.g., a generally fan-shaped beam) and at a low dose (mA) to generate a first set of helical scan projection data 154. The second helical scan may be performed (block 156) with a small or reduced field of view, extended Z-coverage and at a higher dose (mA) relative to the first scan to generate a second set of helical scan projection data 158. In addition, the pitch of the first and second helical scans may differ. For example, the second helical scan may be at a lower pitch relative to the first helical scan. In this example, due to the reduced field of view associated with the second helical scan, the second set of helical scan projection data 158 may be truncated. As discussed above, this data truncation may be addressed using data directly drawn from the first set of helical scan projection data 154 or using a synthesized set of projection data 116 generated using the first set of helical scan projection data 154 and a set or reconstruction (block 110) and reprojection (block 114) steps. Further the synthesized projection data 116 may be used with or combined (block 118) with the second set of helical scan projection data 158, as discussed above, to generate supplemented projection data 120 that may be reconstructed (block 122) to generate a second image 124.

Figure 7:
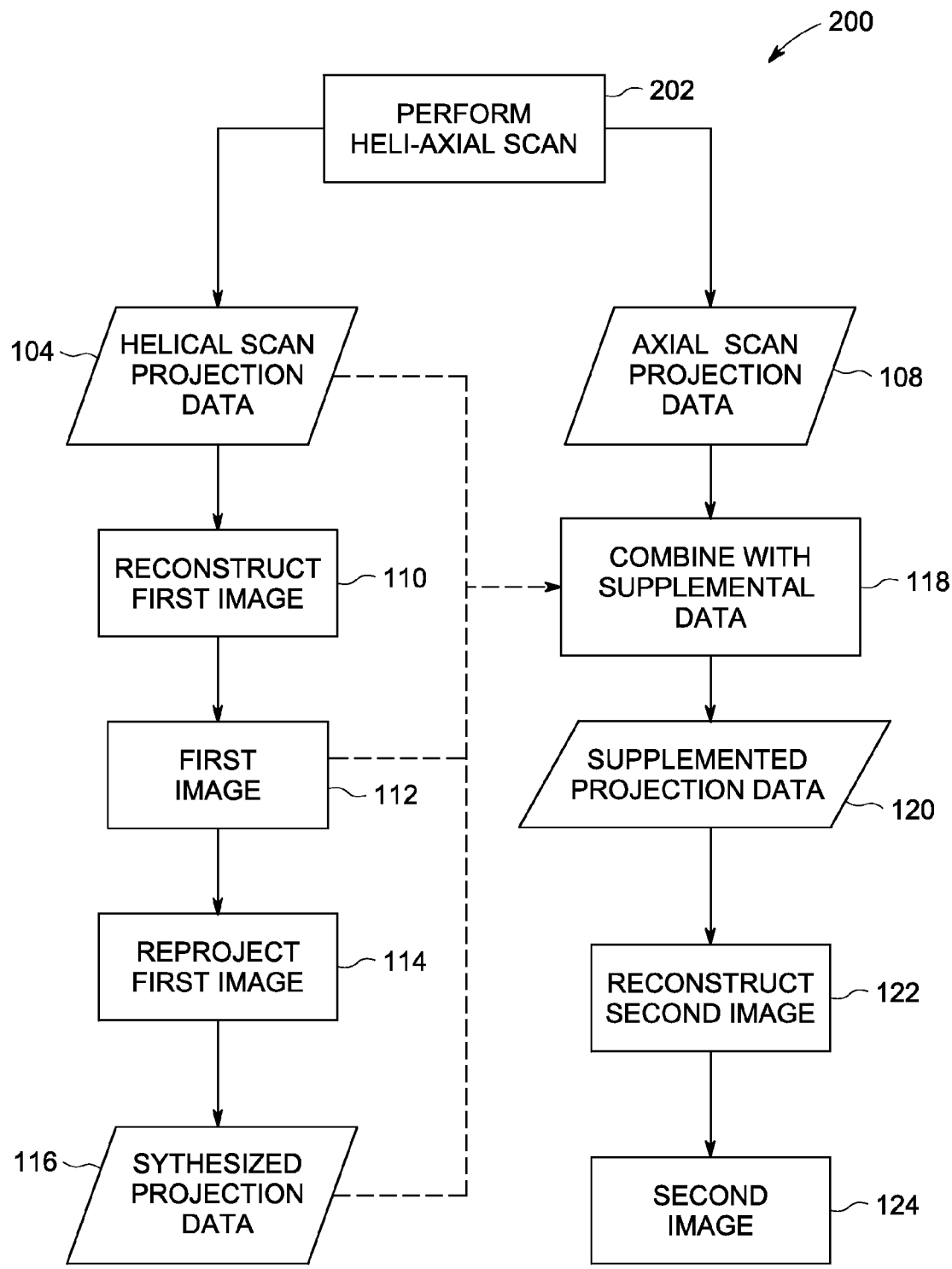
FIG. 7 is a flowchart depicting control logic suitable for implementing a further embodiment of an image acquisition and processing algorithm in accordance with the present disclosure.
Figure 8:
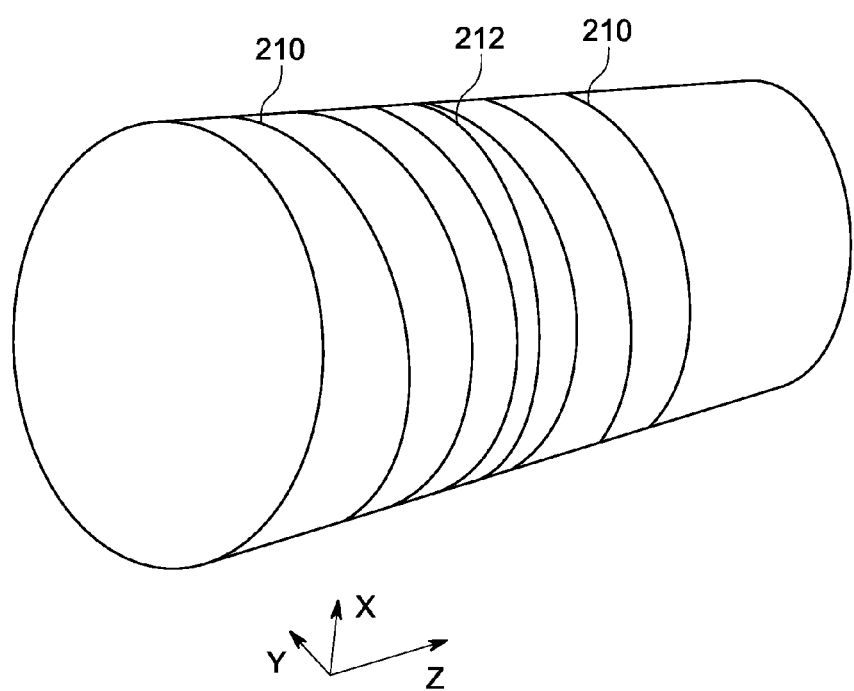
FIG. 8 depicts a scan path for use in accordance with the logic of FIG. 7

While the preceding describe two separate and distinct scans performed as part of an imaging session, it should be appreciated that the different scan protocols may be combined or interleaved into a more unified protocol. For example, turning now to the method 200 depicted in FIGS. 7 and 8, a heli-axial scan protocol is described for use in acquiring both helical and axial projection data for use in accordance with the approaches discussed herein. In accordance with this embodiment, a heli-axial scan is performed (block 202) such that a partial helical scan is performed, followed by one or more axial scans, after which the helical scan is completed, as depicted by the respective helical scan paths 210 and axial scan path 212 in FIG. 8. That is, in accordance with this embodiment, a helical scan is performed up to a point. The helical scan may have constant pitch or variable pitch up to the point (i.e., the translation of the patient table and/or the rotation speed of the source and detector may be constant or may vary). For example, the speed at which the patient table is translated may slow as the point is approached in one embodiment. Once the point is reached, the patient table may be held stationary (or may be moved in increments in accordance with a step-and-shoot axial scan protocol) and a full or partial axial scan may be performed. Once the axial scan is completed, the translation of the patient table is resumed (either at a constant or varying (e.g., increasing) speed) to collect the remainder of the helical projection data. In addition, collimation of the X-rays 16 may be dynamically varied during the heli-axial scan to shape the X-ray beam to the desired field of view and Z-extent at each phase of the heli-axial scan. For example, the X-rays 16 may be shaped to have a wide field of view and a narrow Z-extent during the helical portions of the scan and to have a narrow field of view and a long Z-extent during the axial portion of the scan. In one embodiment, such collimation may be adjusted as the scan occurs such that changes in beam shape are accomplished in a gradual or graded manner as opposed to in a step-wise manner. As a result of the heli-axial scan protocol, both a set of helical scan projection data 104 and axial scan projection data 108 is acquired. The helical scan projection data 104 and the axial scan projection data 108 may be processed as discussed above with respect to FIGS. 5 and 6 to generate the second image 124.

While the preceding describes certain aspects of possible scan protocols, it will be appreciated that other factors may be varied between the first scan and the second scan than those listed above. For example, the first scan may be performed at one energy (kVp) while the second scan is performed at a different energy (kVp). Similarly, one scan (e.g., the first scan) can be performed with kVp switching (i.e., at more than one energy) while the other scan (e.g., the second scan) is performed with a fixed or constant kVp (i.e., at one energy). Further, the first scan may be performed with one type or degree of X-ray filtration while the second scan is performed with a different type or degree of X-ray filtration.

In addition, various alternative embodiments are provided. In one such embodiment, the first scan may be used as a base reconstruction for a compressed sensing or other iterative reconstruction algorithm. In such an embodiment, the second scan can be used to reconstruct a sparse difference image relative to the reconstruction of the first scan.

Further, in multi-energy embodiments the reconstruction from the scan at one energy (such as the helical scan; e.g., the first image in FIG. 5) can be reprojected to the geometry of the second energy scan (such as the axial scan). Subsequently, conventional material decomposition can be applied.

In addition, in an iterative reconstruction embodiment, the first and second scan can both be incorporated into a reconstruction algorithm that uses an accurate forward model for each scan. For example, the forward model for each scan may include geometry, mA, multiple spectra, and so forth).

In another embodiment, the helical scout scan, if employed, can be used to produce accordiographic projections. The accordiographic projections can be used in place of a conventional radiographic scout scan.

Lastly, the second scan can be used to produce a movie or four-dimensional dataset. The movie or four-dimensional dataset may provide a suitable temporal resolution. Further, the movie or four-dimensional dataset may be post-processed to reduce or eliminate noise.

Technical effects of the invention include generating a set of projection data based upon a first set of projection data and a synthetic set of projection data generated using second set of projection data acquired using a different scan protocol. A volumetric representation may be generated using the generated set of projection data. Synthetic projection data may be generated using projection data acquired using helical scan protocol or a heli-axial scan protocol. The first set of projection data and the second set of projection data may be acquired using different portions of a detector, such as different portions of a cross-shaped detector.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring a first set of projection data using a first portion of a detector and a helical scan protocol, wherein an X-ray beam is collimated to a fan shape for the helical scan protocol;
   generating a first volumetric representation using the first set of projection data;
   using the first volumetric representation to configure one or more imaging parameters before acquiring a second set of projection data;
   acquiring the second set of projection data using a second portion of the detector and an axial scan protocol, wherein the first portion is shaped differently than the second portion and the X-ray beam is collimated to a cone shape for the axial scan protocol;
   supplementing the second set of projection data based upon the first set of projection data or data derived using the first set of projection data to generate a supplemented set of projection data; and
   generating a second volumetric representation using the supplemented set of projection data.

2. The method of claim 1, wherein the first set of projection data corresponds to projection data acquired at a first field of view and a first Z-extent and the second set of projection data corresponds to projection data acquired at a second field of view and a second Z-extent.

3. The method of claim 1, wherein the first portion of the detector comprises an elongated portion of the detector and the second portion of the detector comprises a central portion of the detector.

4. The method of claim 1, wherein the detector comprises a cross-shaped or asymmetric detector.

5. The method of claim 1 wherein generating the supplemented set of projection data comprises:
   reprojecting the first volumetric representation based on one or more acquisition parameters associated with the second set of projection data to generate synthesized projection data, some or all of which is used to supplement the second set of projection data.

6. The method of claim 1 wherein the first set of projection data is acquired using a helical portion of a heli-axial scan protocol and the second set of projection data is acquired using an axial portion of the heli-axial scan protocol.

7. The method of claim 1, wherein the first portion and second portion of the detector have one or both of different spatial resolutions or different cell size.

8. The method of claim 1, wherein the imaging parameters comprise one or more of a patient position, an X-ray source voltage, a bowtie filter configuration, a modulation profile, patient dose, or detector view rate.

9. A method, comprising:
   acquiring a set of helical scan projection data using a first portion of a detector and an X-ray beam collimated to a fan shape having a first cone angle;
   generating a first volumetric representation using the helical scan projection data;
   acquiring a set of axial scan projection data using information derived from the first volumetric representation, a second portion of the detector, and an X-ray beam collimated to a cone shape having a second cone angle that is wider than the first cone angle;

generating a set of synthesized data using the set of helical scan projection data;

supplementing the set of axial scan projection data using all or part of the set of synthesized data; and generating a second volumetric representation using the supplemented set of axial scan projection data.

10. The method of claim 9, wherein the set of helical scan projection data and the set of axial scan projection data are acquired using a heli-axial scan protocol.

11. The method of claim 9, wherein the detector comprises a cross-shaped detector.

12. The method of claim 11, wherein the first portion of the detector comprises an elongated portion of the cross-shaped detector and the second portion of the detector comprises a central portion of the cross-shaped detector.

13. The method of claim 9, the information derived from the first volumetric representation comprises one or more of patient position, placement, size, shape, or density.

14. The method of claim 9, wherein using the information derived from the first volumetric representation comprises adjusting one or more acquisition parameters before acquiring the set of axial scan projection data, wherein the acquisition parameters comprise patient position, an X-ray source voltage, a bowtie filter configuration, a modulation profile, patient dose, or detector view rate.

15. The method of claim 9, wherein the first portion and second portion of the detector have one or both of different spatial resolutions or different cell size.

16. One or more non-transitory computer-readable media comprising a code adapted to be executed on a processor, wherein the code comprises:

code that, when executed on the processor, causes a first set of projection data to be acquired using a helical scan protocol, a fan shaped X-ray beam, and a first portion of a detector;

code that, when executed on the processor, causes a second set of projection data to be acquired using an axial scan protocol, a cone shaped X-ray beam, a second portion of the detector, and imaging parameters based upon the first set of projection data, wherein the second portion of the detector differs from the first portion of the detector;

code that, when executed on the processor, causes the second set of projection data to be supplemented using the first set of projection data or data generated using the first set of projection data; and code that, when executed on the processor, causes a volumetric representation to be generated using the supplemented second set of projection data.

17. The one or more non-transitory computer-readable media of claim 16, wherein the detector comprises a cross-shaped detector and the first portion and second portion of the detector have one or both of different spatial resolutions or different cell size.

18. The one or more non-transitory computer-readable media of claim 16, wherein the code that causes the first set of projection data to be acquired when executed on the processor causes a CT scanner to execute a helical portion of a heli-axial scan protocol.

19. The one or more non-transitory computer-readable media of claim 16, wherein the code that causes the second set of projection data to be acquired when executed on the processor causes a CT scanner to execute an axial portion of a heli-axial scan protocol.

20. The one or more non-transitory computer-readable media of claim 16, wherein the code that, when executed on the processor, causes the second set of projection data to be supplemented, generating the set of synthetic projection data by reconstructing a second volumetric representation using the first set of projection data and by reprojecting the second volumetric representation based upon one or more acquisition parameters associated with acquisition of the second set of projection data.

* * * * *